(12) United States Patent
Rubens et al.

(10) Patent No.: US 10,769,498 B2
(45) Date of Patent: *Sep. 8, 2020

(54) IMAGE DATA PRE-PROCESSING

(71) Applicant: KONINKLIJKE PHILIPS N.V., Eindhoven (NL)

(72) Inventors: Eran Rubens, Haifa (IL); Bella Fadida-Specktor, Haifa (IL); Eliahu Zino, Atlit (IL); Menachem Melamed, Haifa (IL); Eran Meir, Haifa (IL); Netanel Weinberg, Haifa (IL); Maria Kaplinsky Nus, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/070,537

(22) PCT Filed: Jan. 25, 2017

(86) PCT No.: PCT/EP2017/051449
§ 371 (c)(1),
(2) Date: Jul. 17, 2018

(87) PCT Pub. No.: WO2017/129573
PCT Pub. Date: Aug. 3, 2017

(65) Prior Publication Data
US 2019/0065904 A1 Feb. 28, 2019

(30) Foreign Application Priority Data

Jan. 25, 2016 (EP) .................................. 16152566
Nov. 24, 2016 (EP) .................................. 16200412

(51) Int. Cl.
*G06K 9/00* (2006.01)
*G06K 9/62* (2006.01)
(Continued)

(52) U.S. Cl.
CPC ......... *G06K 9/6262* (2013.01); *G06K 9/4604* (2013.01); *G06T 5/00* (2013.01);
(Continued)

(58) Field of Classification Search
CPC .... G06K 9/6262; G06K 9/4604; G16H 30/20; G06T 5/00; G06T 11/206; G06T 2207/30004; G06T 2207/20081
(Continued)

(56) References Cited

U.S. PATENT DOCUMENTS 5,235,510 A * 8/1993 Yamada ................ G06F 19/321
600/300
8,160,347 B2 * 4/2012 Chaudhuri ............ G06F 19/321
382/132

(Continued)

FOREIGN PATENT DOCUMENTS

| | | |
|---|---|---|
| CN | 104374872 A | 2/2015 |
| JP | 2009037592 A | 2/2009 |

(Continued)

OTHER PUBLICATIONS

Dantone, M. et al., "Real-time facial feature detection using conditional regression forests", Computer Visiion adn Pattern Recognition (CVPR), 2012 IEEE Conference on, IEEE, (Jun. 16, 2012), pp. 2578-2585.

(Continued)

*Primary Examiner* — Marceau Milord

(57) ABSTRACT

A computer-implemented method (40) reduces processing time of an application for visualizing image data, which application is one of a plurality of applications selectable by a user. Each of the plurality of applications includes a pre-processing algorithm for pre-processing the image data. The method predicts which one of the pre-processing algorithms is to be performed in response to a selection of an (Continued)

application by the user by: —extracting a feature vector from the image data, metadata, and/or additional data associated with the image data, —supplying the feature vector as input to a machine learned model, and —receiving an algorithm identifier as output from the machine learned model. The algorithm identifier identifies the pre-processing algorithm. Additionally, the algorithm identifier is used to select (42) the pre-processing algorithm. The image data is pre-processed (43) using the selected pre-processing algorithm.

18 Claims, 5 Drawing Sheets

(51) Int. Cl.
*G06T 5/00* (2006.01)
*G06K 9/46* (2006.01)
*G06T 11/20* (2006.01)
*G16H 30/20* (2018.01)

(52) U.S. Cl.
CPC .......... *G06T 11/206* (2013.01); *G16H 30/20* (2018.01); *G06T 2207/20081* (2013.01); *G06T 2207/30004* (2013.01)

(58) Field of Classification Search
USPC .................................................. 382/128, 250
See application file for complete search history.

(56) References Cited

U.S. PATENT DOCUMENTS

| | | | | |
|---|---|---|---|---|
| 8,165,368 B2* | 4/2012 | Vijaykalyan | .......... | G06F 19/321 382/128 |
| 8,321,367 B2* | 11/2012 | Nishida | .................. | G06Q 10/10 382/159 |
| 8,526,693 B2 | 9/2013 | Vijaykalyan et al. | | |
| 8,718,376 B2* | 5/2014 | Yim | ........................ | G06T 5/001 382/190 |
| 8,872,822 B2* | 10/2014 | Ekin | ..................... | G06T 7/0012 345/424 |
| 8,923,580 B2 | 12/2014 | Dekel et al. | | |
| 8,965,104 B1* | 2/2015 | Hickman | .................. | G06T 7/00 382/153 |
| 9,275,307 B2* | 3/2016 | Chattopadhyay | ........ | G06K 9/34 |
| 10,163,028 B2* | 12/2018 | Rubens | ................ | G06K 9/4604 |
| 2006/0224539 A1* | 10/2006 | Zhang | ..................... | G06K 9/623 706/20 |
| 2007/0076934 A1* | 4/2007 | Krishnan | .............. | G06F 19/321 382/128 |
| 2007/0133851 A1* | 6/2007 | Sirohey | ................. | G06F 19/321 382/128 |
| 2007/0196013 A1* | 8/2007 | Li | ...................... | G06K 9/00456 382/159 |
| 2007/0219729 A1* | 9/2007 | Peligrad | .................... | G06T 7/20 702/25 |
| 2008/0025583 A1* | 1/2008 | Jabri | ........................ | G06T 5/00 382/128 |
| 2008/0069419 A1* | 3/2008 | Farag | .................... | G06T 19/003 382/131 |
| 2010/0014755 A1* | 1/2010 | Wilson | ............... | G06K 9/00604 382/173 |
| 2011/0172514 A1* | 7/2011 | Lee | ...................... | G06K 9/6262 382/128 |
| 2012/0189180 A1* | 7/2012 | Yeluri | .................... | G06F 19/321 382/128 |
| 2013/0129198 A1* | 5/2013 | Sherman | ............... | G06F 19/321 382/159 |
| 2013/0243298 A1* | 9/2013 | Bredno | ..................... | G06T 5/50 382/131 |
| 2013/0315479 A1* | 11/2013 | Paris | .................... | G06K 9/6256 382/159 |
| 2014/0348420 A1* | 11/2014 | Chattopadhyay | ........ | G06K 9/34 382/159 |
| 2015/0160836 A1 | 6/2015 | Lafreniere et al. | | |
| 2015/0265224 A1* | 9/2015 | Gerland | ................. | A61B 6/032 382/131 |
| 2016/0062956 A1 | 3/2016 | Shlomo et al. | | |
| 2016/0166209 A1* | 6/2016 | Itu | .......................... | A61B 5/026 600/408 |
| 2016/0203263 A1* | 7/2016 | Maier | ................... | G06F 19/321 705/2 |
| 2016/0378919 A1* | 12/2016 | McNutt | ................. | G06Q 50/24 705/3 |
| 2017/0213101 A1* | 7/2017 | Rubens | ................ | G06K 9/4604 |

FOREIGN PATENT DOCUMENTS

| | | |
|---|---|---|
| JP | 2009296140 A | 12/2009 |
| WO | 2007129813 A1 | 11/2007 |

OTHER PUBLICATIONS

Breiman, L. "Random forest", Machine learning, 45(1), 5-32, (2001).
Baeza-Yates, R and Ribeiro-Neto, B. "Modern information retrieval", vol. 463. New York: ACM press (1999).
Chamchong, R. et al., "Optimal selection of binarization techniques for the processing of ancient palm leaf manuscripts", Systems Man and Cybernetics (SMC), 2010 IEEE International Conference on, N.J. (Oct. 10, 2010), pp. 3796-3800.
Chattopad T. et al.,: "Automatic Selection of binarization method for Robust OCT", 2013 12th International Conference on Document Analysis and Recognition, IEEE, Aug. 25, 2013, pp. 1170-1174.

* cited by examiner

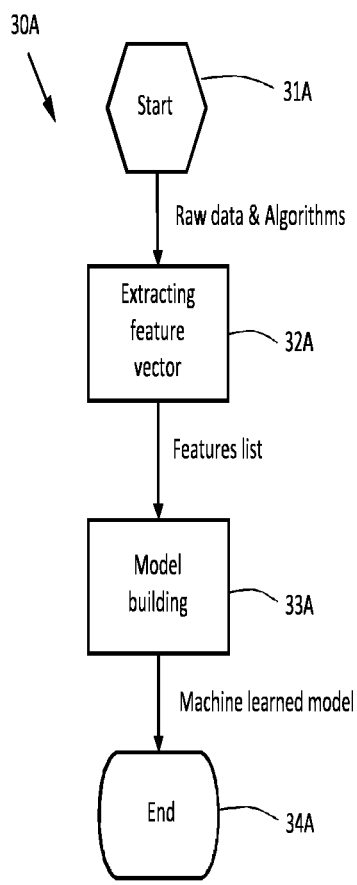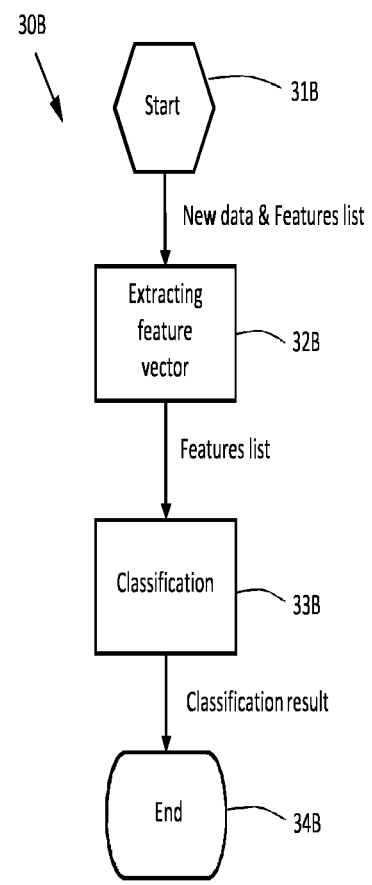
Fig. 3A
Fig. 3B

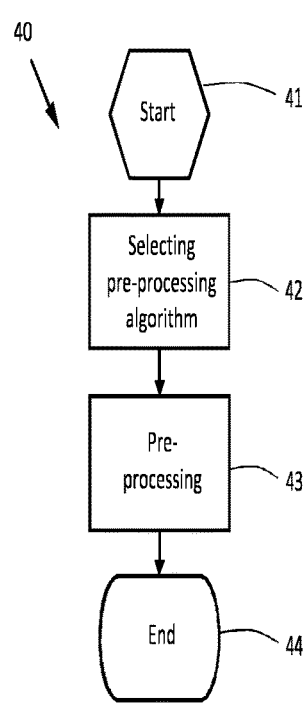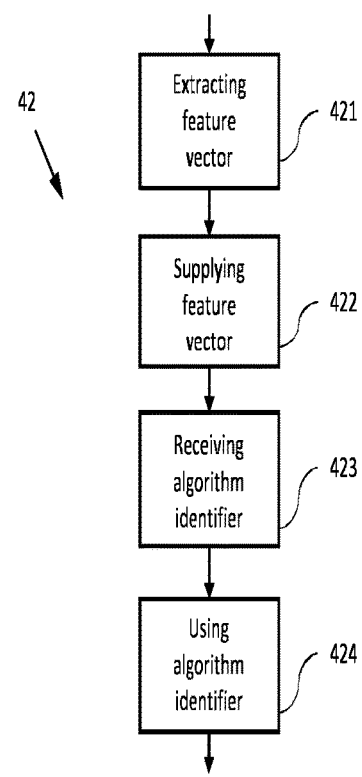
Fig. 4A
Fig. 4B

IMAGE DATA PRE-PROCESSING

CROSS-REFERENCE TO PRIOR APPLICATIONS

This application is the U.S. National Phase application under 35 U.S.C. § 371 of International Application No. PCT/EP2017/051449, filed on Jan. 25, 2017, which claims the benefit of European Patent Application No. 16152566.2, filed on Jan. 25, 2016 and European Patent Application No. 16200412.1, filed on Nov. 24, 2016. These applications are hereby incorporated by reference herein.

FIELD OF THE INVENTION

The present invention relates to a device and a computer-implemented method for pre-processing image data. The present invention further relates to a computer readable medium comprising instructions for causing a processor system to perform the method. The present invention also relates to a workstation or imaging apparatus comprising the device.

BACKGROUND OF THE INVENTION

It is well known to process image data in preparation of displaying an image. Image data may be processed to enhance an image in various ways, for example to improve the contrast of the image or to highlight or select part of the image. So-called advanced visualization (AV) applications allow more advanced image processing, for example for image manipulation. In medical applications, for example, advanced visualization may provide 3D views or sliced views, or may provide measurement data. Here, the term 'advanced' is used to distinguish the visualization application from, for example, a standard Picture Archiving and Communication System (PACS) viewer as it provides improved or additional functionality. For example, a doctor may want to produce a certain set of views of part of the body, and may want to improve the contrast and/or change the colors in some of those views. In such a case, a doctor may use two or more advanced visualization applications for a single set of image data, to produce two or more advanced visualization views.

International patent application WO 2014/174461 (US 2016/0062956A1), the entire contents of which are herewith incorporated in this document, discloses a method of image visualization which includes capturing a visual context of an image study displayed using a basic visualization application, identifying the image study, loading the image study on a visualization computing system, and launching an advanced visualization application. In WO 2014/174461, an advanced visualization application is described as an application with image viewing and/or image manipulating capabilities that are not common across computing systems and/or are not part of a basic visualization application.

When using advanced visualization applications, the problem arises that such applications typically involve a very large number of computations, thus requiring a substantial processing time. Some advanced visualization applications initially perform processing of the image data and may therefore take a long time from their activation before being fully operational. If two or more advanced visualization applications are to be used to produce views of a single set of image data, the delay introduced by the processing being carried out upon activation of the applications increases. European patent application EP 2 172 860 (US 2014/0348420A1) discloses a method for determining a hanging protocol for display of clinical images in an image study. A hanging protocol typically is a set of actions to arrange images for viewing in a picture archiving and communication system (PACS). The method of EP 2 172 860 includes classifying an image study based on a combination of high level characteristics and low level characteristics of the image study, and determining a hanging protocol for the image study based on the classifying. EP 2 172 860 does not concern advanced visualization applications and offers no solution for the long delays when starting up such applications.

SUMMARY OF THE INVENTION

It is an object of the present invention to solve this problem by providing a method and device which allow advanced visualization applications and similar applications for visualizing image data to be more rapidly available. Accordingly, the present invention provides a computer-implemented method of reducing processing time of an application for visualizing image data, wherein the application is one of a plurality of applications selectable by a user, wherein each of the plurality of applications comprises a pre-processing algorithm for pre-processing the image data, wherein the method comprises predicting which one of the pre-processing algorithms is to be performed in response to a selection of an application by the user by:

- extracting a feature vector from the image data, metadata, and/or additional data associated with the image data,
- supplying the feature vector as input to a machine learned model, and
- receiving an algorithm identifier as output from the machine learned model, the algorithm identifier identifying the pre-processing algorithm, the method further comprising:
- using the algorithm identifier to select the pre-processing algorithm, thereby obtaining a selected pre-processing algorithm, and
- pre-processing the image data using the selected pre-processing algorithm. By pre-processing image data, the processing required by the actual advanced visualization processing can be reduced and pre-processing at the start-up of advanced visualization applications can be avoided, thus significantly shortening their start-up time. However, if a set of pre-processing algorithms (or pre-processing applications) is available, it has to be decided which pre-processing algorithm to use. Typically, for a certain advanced visualization application a specific pre-processing algorithm is required, although a single pre-processing algorithm may be suitable for several advanced visualization applications. However, the requirement of a specific pre-processing algorithm makes it necessary to select the pre-processing algorithm well before starting the advanced visualization application.

It is noted that selecting a pre-processing algorithm may amount to predicting which advanced visualization algorithm will be selected, for example by an operator, and selecting the pre-processing algorithm associated with the particular advanced visualization algorithm.

By using a machine learned model when selecting at least one pre-processing algorithm or application, the selection process can be made simpler and faster, thus saving time. The machine learned model can be configured to provide at least a recommendation based on the image data to be pre-processed, or on the associated (image data related)

metadata. More in particular, using a machine learned model may involve providing the image data, (image data related) metadata and/or any additional (image data related) information (such as a radiology report or a medical record) to the machine learned model, and receiving a recommendation from the machine learned model.

In an embodiment, the machine learned model provides a selection recommendation, which recommendation is presented to a user. More in particular, using the algorithm identifier to select a pre-processing algorithm may further comprise:

presenting the algorithm identifier to a user,
receiving user input from the user, and
supplying the user input to the set of pre-processing algorithms to initiate a pre-processing algorithm corresponding with the user input.

That is, the machine learned system recommends a selection but leaves the actual selection to the user(s). This embodiment provides a machine-assisted selection of pre-processing algorithms. The user input may be a confirmation or a rejection of the presented algorithm identifier. In case of a confirmation, the user input supplied to the set of pre-processing algorithms may include the algorithm identifier presented to the user. In case of a rejection, the user input supplied to the set of pre-processing algorithms may include another algorithm identifier supplied by the user. Accordingly, supplying the user input to the set of pre-processing algorithms to initiate a pre-processing algorithm corresponding with the user input may include supplying the presented algorithm identifier or supplying an alternative algorithm identifier chosen by the user.

In another embodiment, the machine learned model provides a selection. More in particular, using the algorithm identifier to select a pre-processing algorithm may further comprise supplying the algorithm identifier to the set of pre-processing algorithms to initiate a pre-processing algorithm corresponding with the identifier. That is, in this embodiment the selection process can be fully automated, requiring no human intervention.

It is preferred that the machine learned model is produced by a machine learning system, preferably a dynamic supervised machine learning system. Dynamic supervised machine learning systems can learn from image data of a specific site (for example the image data of a particular hospital) and adapt to changes over time in the image data of that particular site. In contrast, in offline learning the machine learned model is trained once for all relevant sites, and is not adapted to a particular site. Because of the variability in the image data between different sites (for example different protocols, different languages, and/or different scanners), a dynamic system is typically preferred.

In an embodiment, the machine learning system comprises a machine learning engine configured for building a machine learned model by using a feature vector as input vector and receiving at least one algorithm identifier as output vector, wherein the feature vector is extracted from the image data, metadata, and/or additional data associated with the image data. By using a machine learning engine configured for building a machine learned model, a suitable model can be provided to facilitate the selection of the at least one pre-processing algorithm.

The feature vector may be extracted from the image data, metadata, and/or additional data associated with the image data from a single picture archiving and communication system. That is, the feature vector and hence the machine learned model may relate to a single image storing system, for example the image storage system of a single hospital or group of hospitals. This makes it possible to provide a dedicated machine learned model based on local image data.

The image data may relate to medical images, while the metadata may comprise at least one of DICOM (Digital Imaging and Communications In Medicine) data, text data, text metadata and/or patient related information. DICOM data may include DICOM headers. In an embodiment, selecting the al least one pre-processing algorithm may comprise extracting a feature vector from DICOM data, such as a DICOM header. In a further embodiment, the feature vector may be identical to the DICOM data, such as the DICOM header. In another further embodiment, the feature vector may be identical to text data associated with an image or set of images, or to text metadata associated with an image or with a set of images.

The present invention also provides a method of processing image data, the method comprising the steps of pre-processing the image data as described above, and advanced visualization processing the pre-processed image data. More in particular, the invention provides a method of processing image data, the method comprising carrying out a method of pre-processing image data using a pre-processing algorithm selected by a machine learned model, and using an advanced visualization processing application to further process the pre-processed image data. The method may comprise receiving user input, and using a second pre-processing algorithm selected by the user input if the first pre-processing algorithm selected by the machine learned model fails to match the user input.

It is noted that the pre-processing algorithm is initiated before the advanced visualization processing application is initiated. Preferably, the advanced visualization processing application is initiated after the pre-processing algorithm has terminated. However, it is also possible to initiate the advanced visualization processing application while the pre-processing algorithm is still running, as this will still result in a reduction of the overall processing time. As described above, if the initiated pre-processing algorithm fails to match the advanced visualization application initiated by a user, then another pre-processing algorithm may be automatically initiated. This other or second pre-processing algorithm may be automatically initiated in response to users input.

In some embodiments, a pre-processing algorithm can be configured for leaving the image data unaltered. That is, at least one pre-processing algorithm of the set of pre-processing algorithms may be configured for not changing the image data. Such a "null algorithm" can be used if no pre-processing is required, or if no or not sufficient pre-processing resources are available at a certain point in time. It will be understood that using a "null algorithm" that leaves the image data unaltered amounts to not pre-processing the image data at all. Effectively, in such embodiments the method of the present invention can be said to be a method of determining whether a pre-processing algorithm is to be applied to the image data, and if a pre-processing algorithm is to be applied, determining which pre-processing algorithm is (or which pre-processing algorithms are) to be applied, while if a pre-processing algorithm is not to be applied, omitting applying the pre-processing algorithm.

The present invention further provides a software program product comprising instructions allowing a processor to carry out the method described above. The software program product may be stored on a tangible carrier, such as a DVD or a USB stick. Alternatively, the software program product may be stored on a server from which it may be downloaded using the Internet. The software program product contains software instructions which can be carried out by the processor of a device, such as a server, an imaging device, and/or a monitoring device. The software program product may alternatively be described as a computer readable medium comprising transitory or non-transitory data representing instructions arranged to cause a processor to carry out the method described above. The present invention still further provides a device configured for reducing processing time of an application for visualizing image data, wherein the application is one of a plurality of applications selectable by a user, wherein each of the plurality of applications comprises a pre-processing algorithm for pre-processing the image data, the device comprising:

an input interface configured to access the image data, metadata, and/or additional data associated with the image data;

a memory comprising application data representing the plurality of applications and instruction data representing a set of instructions; and a processor configured to communicate with the input interface and the memory and to execute the set of instructions, wherein the set of instructions, when executed by the processor, cause the processor to predict which one of the pre-processing algorithms is to be performed in response to a selection of an application by the user by:

extracting a feature vector from the image data, metadata, and/or additional data associated with the image data, supplying the feature vector as input to a machine learned model, wherein the machine learned model is stored as model data in the memory, and receiving an algorithm identifier as output from the machine learned model, the algorithm identifier identifying the pre-processing algorithm;

the set of instructions, when executed by the processor, further causing the processor to:

use the algorithm identifier to select the pre-processing algorithm, thereby obtaining a selected pre-processing algorithm, and pre-process the image data using the selected pre-processing algorithm.

The device has similar advantages to the method described above. The device may further comprise a storage unit configured to store pre-processing algorithms and to retrieve a stored pre-processing algorithm in response to the selection information, and/or a selection unit for receiving selection input from a user and combining the selection input with the selection information to select an algorithm. The device may be a workstation or an imaging apparatus.

The present invention additionally provides an image processing system comprising an advanced visualization processing device, and a device configured for reducing processing time as described above. The image processing system may further comprise a storage device for storing image data, and a display device for displaying image data.

It will be appreciated by those skilled in the art that two or more of the above-mentioned embodiments, implementations, and/or optional aspects of the invention may be combined in any way deemed useful.

Modifications and variations of the workstation, the imaging apparatus, the system, and/or the computer program product, which correspond to the described modifications and variations of the computer-implemented method, can be carried out by a person skilled in the art on the basis of the present description, and vice versa.

BRIEF DESCRIPTION OF THE DRAWINGS

The present invention will further be explained with reference to exemplary embodiments illustrated in the drawings, in which:

FIGS. 3A and 3B schematically show exemplary embodiments of a training phase and a classification phase of a machine learning system as may be used in the present invention.

FIGS. 4A and 4B schematically show an exemplary embodiment of a method according to the present invention.

DETAILED DESCRIPTION OF EMBODIMENTS

The present invention allows advanced visualization processing of image data to be carried out more rapidly by pre-processing image data in preparation of advanced visualization processing, and to assist a user in selecting one or more pre-processing algorithms on the basis of the image data to be pre-processed. To this end, the invention uses a machine learned model, provided by a machine learning system, to assist in selecting a pre-processing algorithm.

Advanced visualization is a term well known in the art and may involve image viewing and/or image manipulation capabilities not found in basic visualization. Advanced visualization (AV) typically produces additional data relating to images, the additional data being the result of applying certain algorithms to the image data. Accordingly, some forms of advanced visualization may be described as a type of image processing which utilizes additional processing to produce additional data relating to the image. The additional data may allow a user to see more information and/or to measure items in the image more effectively.

The pre-processing mentioned in this document may include the actual advanced visualization processing, any preparation of image data for subsequent advanced visualization processing, or both. In all cases, the pre-processing serves to save processing time when an advanced visualization application is used.

Figure 1:
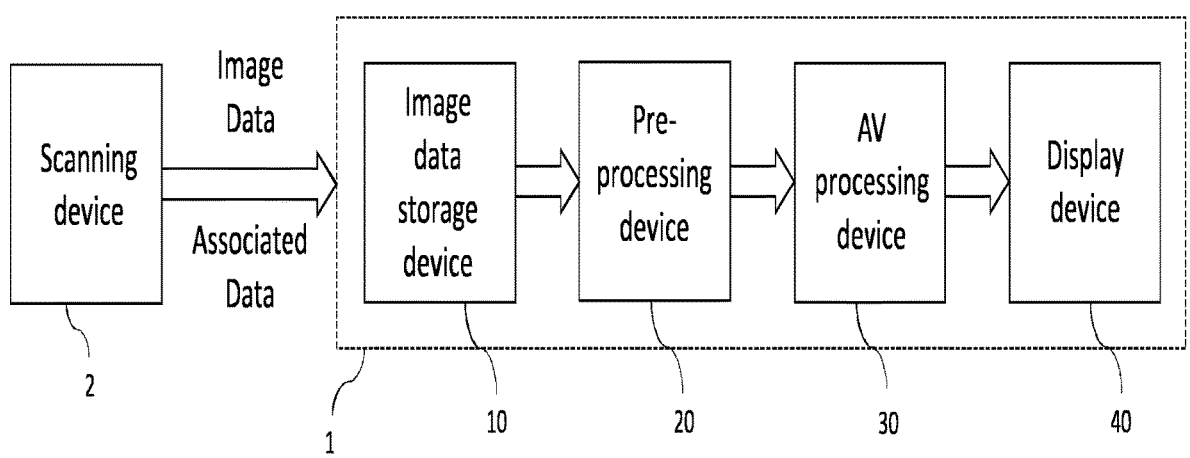
FIG. 1 schematically shows an exemplary embodiment of an image processing system according to the present invention.

An image processing system according to the present invention is schematically illustrated in FIG. 1. The image processing system 1 of FIG. 1 comprises an image data storage device 10, a pre-processing device 20, a processing device 30 and a display device 40. The image processing system 1 is in the embodiment shown connected to a scanning device 2.

The scanning device or scanner 2 may be a CT (computer tomography) scanner, an MR (magnetic resonance) scanner, an X-ray scanner or any other suitable type of scanner. In some embodiments, the image data may be produced by a camera. The scanning device 2 may produce metadata, such a scan numbers, and associate any metadata with the image data. Metadata and/or any additional data, such as patient records, may also be derived from other sources (not shown in FIG. 1), such as hospital computer systems or other data systems, such as RIS (Radiology Information System) or EMR (Electronic Medical Record).

The image data storage device 10 is configured for storing image data and associated metadata and additional data received from the scanning device 2 or from other sources, and for providing image data and associated additional data and/or metadata to the pre-processing device 20.

Figure 2:
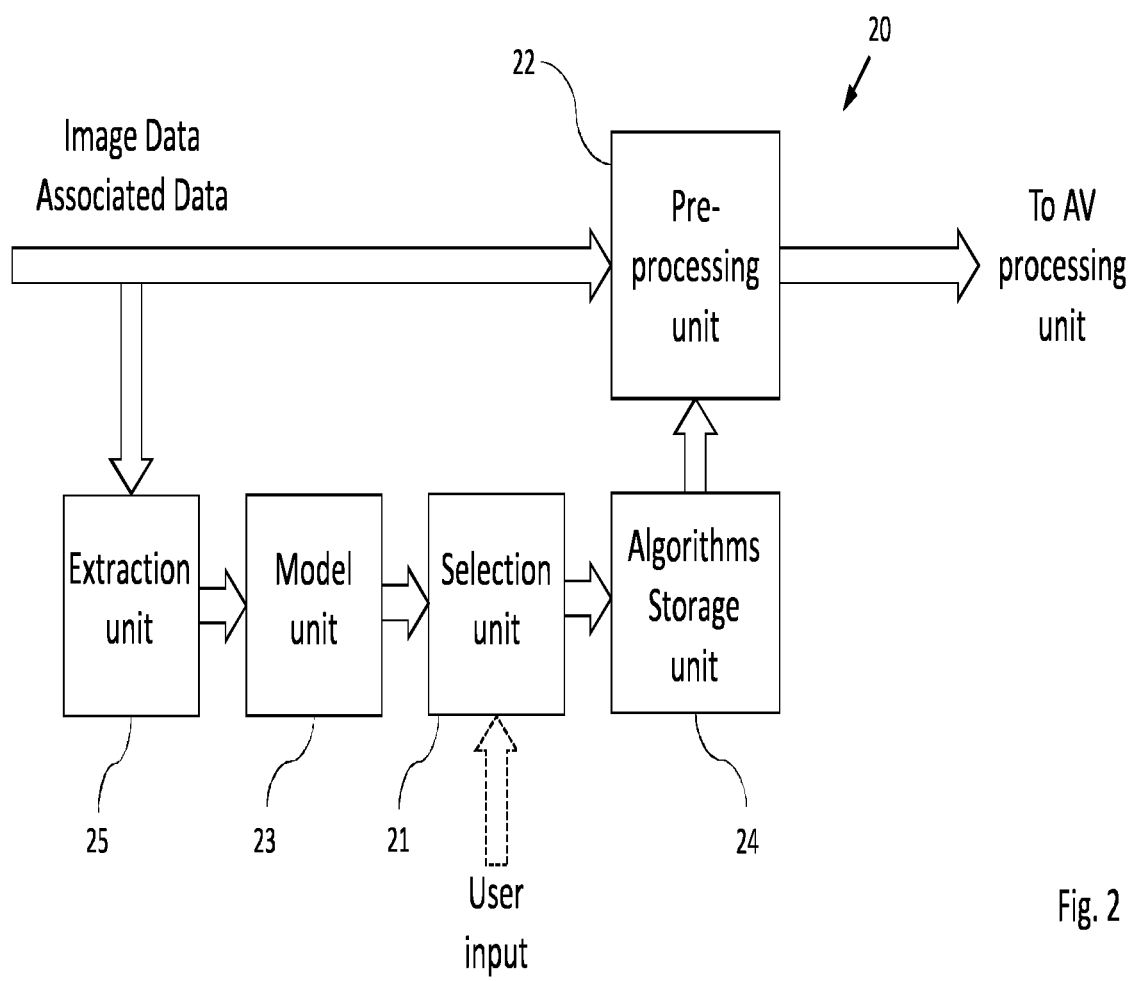
FIG. 2 schematically shows an exemplary embodiment of a device for pre-processing image data according to the present invention.

The pre-processing device 20, which will later be discussed in more detail with reference to FIG. 2, is configured for receiving image data and associated data from the image data storage device 10 and for pre-processing the received image data by using a suitable pre-processing algorithm. According to the invention, the suitable pre-processing algorithm is chosen from a set of pre-processing algorithms with the assistance of a machine learned model.

The AV (advanced visualization) processing device 30 can be configured for advanced visualization processing or another type of image data processing which prepares image data for rendering on a display device, such as the display device 40 shown in FIG. 1. In the field of medicine, AV processing can provide measurements of body parts, 3D views of the body or of part of the body, and other valuable information. However, AV processing applications typically require a large amount of processing, which is time consuming, even on fast workstations. Some AV applications require running a specific algorithm beforehand to prepare the image data for the AV application. This can result in a long waiting time before the actual AV application can start.

In order to reduce this delay, the present invention provides pre-processing of the image data by using a pre-processing application which is selected with the aid of a machine learned model. This will be further explained with reference to FIG. 2.

In FIG. 2, an embodiment of the pre-processing device 20 illustrated in FIG. 1 is shown in more detail. The exemplary embodiment of FIG. 2 is shown to comprise a selection unit 21, a pre-processing unit 22, a model unit 23, an algorithm storage unit 24 and a feature extraction unit 25. The pre-processing unit 22 is configured to receive image data from any previous units, such as the image data storage unit 10 shown in FIG. 1. The feature extraction unit 25 is also configured to receive image data and any associated metadata from a previous unit. More in particular, the feature extraction unit 25 can be configured to extract a feature vector from the image data and/or any associated data and to supply this feature vector as input to a machine learned model stored in the model unit 23.

An alternative embodiment to the embodiment of FIG. 2 may be the following device. Here, the function of the extraction unit, the model unit, the selection unit and/or the pre-processing unit may be performed by a processor. The device may comprise an input interface configured to access the image data, metadata, and/or additional data associated with the image data. For example, the input interface may be a network interface to a Picture Archiving and Communication System (PACS) of a Hospital Information System (HIS) to which the device may be connected or comprised in. In general, the input interface may take various forms, such as a network interface to a local or wide area network, e.g., the Internet, a storage interface to an internal or external data storage, etc.

The device may comprise a processor configured to internally communicate with the input interface via internal data communication, and a memory accessible by the processor via internal data communication. The memory may comprise application data representing the plurality of applications and instruction data representing a set of instructions. The processor may be configured to predict, during operation of the device, which one of the plurality of applications is to be selected by the user by extracting a feature vector from the image data, metadata, and/or additional data associated with the image data, supplying the feature vector as input to a machine learned model, wherein the machine learned model is stored as model data in the memory, and receiving an application identifier as output from the machine learned model, the application identifier identifying the application. The set of instructions, when executed by the processor, may further cause the processor to use the application identifier to select the processing algorithm associated with the application, and pre-process the image data using the selected processing algorithm.

The above described device may be embodied as—or in—an apparatus, such as a workstation or imaging apparatus. The device or apparatus may comprise one or more (micro)processors which execute appropriate software. The processor of the device or apparatus may each be embodied by one or more of these (micro)processors, or by a same (micro)processor. Software implementing the functionality of the device, may have been downloaded and/or stored in a corresponding memory or memories, e.g., in volatile memory such as RAM or in non-volatile memory such as Flash. Alternatively, the processor of the device may be implemented in the form of programmable logic, e.g., as a Field-Programmable Gate Array (FPGA). The input interface may be implemented by respective interfaces of the device or apparatus. In general, each unit of the devices described in this specification may be implemented in the form of a circuit. It is noted that the device may also be implemented in a distributed manner, e.g., involving different devices or apparatuses.

In an embodiment, a Bag-of-Words data representation can be used for feature processing and extraction. However, the invention is not so limited and other methods may be used instead.

The machine learned model of the model unit 23 produces as output an image data classification identifier, which identifies a class of image data of an available set of image classes. The image data classification identifier is fed to the selection unit 21. In response to the received image data classification identifier, the selection unit 21 produces an algorithm identifier and feeds this algorithm identifier to the storage unit 24. The selection unit 21 therefore maps image data classification identifiers onto algorithm identifiers. It is noted that in some embodiments, the machine learned model of model unit 23 may already produce algorithm identifiers, in which case the function of the selection unit 21 may be limited to allowing user interaction. It is further noted that the classifier may include a Random Forest, an SVM (Support Vector Machine), a neural network, a boosting type classifier, or a combination of two or more of these classifiers, for example. However, it will be understood that the invention is not limited to these classifiers.

In some embodiments, the selection unit 21 is configured for receiving user input, that is, user selection information. This user input can be limited to accepting or rejecting an algorithm identifier (or an image data classification identifier) produced by the selection unit 21 (or the model unit 23 respectively) and presented as recommendation to a user. To provide a recommendation, the selection unit 21 may be provided with a display screen which displays the algorithm identifier (or the image data classification identifier).

A user may confirm the selection recommendation (that is, the algorithm identifier and/or image data classification identifier) provided by the selection unit 21, or may overrule this selection recommendation by inputting another algorithm identifier or its equivalent. In some embodiments, the selection unit 21 may provide more than one selection recommendation, for example two or three selection recommendations, from which the user is to choose one. Multiple selection recommendations may in particular be offered when the output of the machine learned model is inconclusive. Selection recommendations may be presented to a user together with respective confidence levels provided by the machine learned model.

It is noted that in embodiments in which the selection unit 21 is not configured for receiving user input, the algorithm selection can be fully automatic.

The storage unit 24 uses the received algorithm identifier to select a suitable pre-processing algorithm from a set of pre-processing algorithms stored in the storage unit 24. The storage unit 24 then feeds the selected pre-processing algorithm to the pre-processing unit 22 for pre-processing the image data by using the selected pre-processing algorithm. The pre-processed image data are then fed to an AV processing unit (30 in FIG. 1) or any other suitable image data processing unit.

The pre-processing unit 20 according to the invention is capable of pre-processing image data and selecting a suitable pre-processing algorithm, based upon the image data and/or any associated data, such as image metadata and DICOM data (DICOM=digital imaging and communications in medicine). The DICOM data that may be used may include a DICOM header. Image metadata may include text data and/or text metadata.

In some embodiments, the pre-processing unit 22 may be capable of applying two or more pre-processing algorithms to a single set of image data, and of buffering the two or more pre-processed sets of image data. If the pre-processing carried out on one of the sets of image data matches the subsequent AV processing, then that set of pre-processed image data is used for AV processing and any other sets are discarded. If none of the sets of image data matches the subsequent AV processing, then all sets are discarded.

As mentioned above, a pre-processing algorithm may be configured for leaving the image data unaltered. That is, at least one pre-processing algorithm of the set of pre-processing algorithms may be configured for not changing the image data. Such a "null algorithm" can be used if no pre-processing is required, or if no or not sufficient pre-processing resources are available at a certain point in time. It will be understood that using a "null algorithm" that leaves the image data unaltered amounts to not pre-processing the image data at all. Effectively, in such embodiments the method of the present invention can be said to be a method of determining whether a pre-processing algorithm is to be applied to the image data, and if so, which pre-processing algorithm is (or which pre-processing algorithms are) to be applied.

It is noted that a pre-processing algorithm is carried out by a pre-processing software application, and that the terms algorithm and application may generally be interchanged in this document. It is further noted that the term pre-processing relates to processing which takes place before, and in preparation of, the actual processing.

FIGS. 3A and 3B schematically show exemplary embodiments of a training phase and a classification phase are used in the present invention. The training of the machine learned model preferably is supervised training.

The training of a model is schematically illustrated in FIG. 3A. The exemplary model training method 30A comprises a start step 31A in which the method is initiated. Raw data and "ground truth" constituted by suitable pre-processing algorithms and/or associated classifications are used in step 32A, in which a feature vector is extracted from the raw data. The raw data may comprise image data, image metadata and/or additional data associated with the image data. The image data may be medical image data, such as images produced during medical scans, for example MRI (Magnetic Resonance Imaging) scans.

The feature vector is fed to a model as a list of features. In step 33A a model is produced using machine learning. When a machine learned model is obtained, the method ends in step 34A.

Once the machine learned model is obtained, it can be used to classify image data, as is schematically illustrated in FIG. 3B. The exemplary image classification method 30B illustrated in FIG. 3B comprises a start step 31B, in which the method is initiated. In step 32B, new data (in contrast to the training data used in the training method 30A of FIG. 3A) and a features list are input to the machine learned model to extract a feature vector from the image data (and any associated data, such as metadata). The machine learned model outputs a feature vector or features list which is used in step 33B to classify the image data. That is, based on the features contained in the feature vector or the features list, the image data are assigned to a certain class of a set of classes. The classification result allows a pre-processing algorithm to be selected, as a specific (but not necessarily unique) pre-processing algorithm can be assigned to each of the classes. The method ends in step 34B, but may be repeated for new image data.

The method of the present invention is illustrated in FIG. 4A. The embodiment of the method 40 shown in FIG. 3 starts with an initial step 41, in which the method is initialized. In step 42, a pre-processing algorithm (typically a pre-processing application) is selected. Subsequently, in step 43, the pre-processing of the image data is carried out using the selected pre-processing algorithm. The method ends in step 44. It will be understood that the embodiment of FIG. 4A is only exemplary and that other embodiments of the method according to the invention can be envisaged.

Step 42 of the method of FIG. 4A is illustrated in more detail in FIG. 4B. In the embodiment of FIG. 4, the "selecting pre-processing application" step 42 of FIG. 3 is shown to comprise an "extracting feature vector" step 421, a "supplying feature vector" step 422, a "receiving application identifier" step 423, and a "using application identifier" step 424.

In step 421, a feature vector is extracted from the image data and/or from any associated data, such as metadata (for example an image frame number) or additional data, such as a patient's medical record. In step 422, this feature vector is supplied to a machine learned model. In response to this input vector, the machine learned model produces an output vector, also known as answer vector, which contains an algorithm identifier. In step 424, the algorithm identifier is used to select an algorithm from the available set of algorithms (which can be stored in the algorithms storage unit 24 in FIG. 2).

It is noted that the machine learned model may not directly produce an algorithm identifier, but that the algorithm identifier is derived, for example by the selection unit 21 shown in FIG. 2, from the output vector of the machine learned model.

In some embodiments, the feature vector or classifier may be extracted from DICOM metadata, and in particular from a DICOM header of the image data. Such a DICOM header may comprise DICOM text tags, and in particular free-text DICOM tags. Here, the term 'free-text' may refer to unstructured rather than structured text. In these embodiment, a multi-class supervised machine learning approach may be used to predict which algorithm needs to be applied on the data. The input to the algorithm may be a set of free-text DICOM tags from a given series, and the output may be a pre-processing algorithm that needs to be applied or "NONE" in case no pre-processing is needed. Firstly a feature processing may be performed on the input, and then resulted features may be fed to a classifier. For feature processing, a 2-Gram Bag of Words (BOW) data representation may be used. The BOW features may be learned on-site, adapting to the data specifics of the hospital.

The feature processing pipeline may comprise one or more of the following:
  Data cleaning and transformation. The listed text DICOM tags may be transformed to lowercase and unnecessary characters (such as %, (,), [ ], +) may be removed. To account for possible meaningful numbers, two sets may be created—one with removed numbers and the other untouched. The sets may be united later on.
  Words extraction. Unigrams and Bigrams may be extracted from both sets and for all text tags.
  Words Filtering. Words with 1 letter may be removed and only terms with frequency above 2 may be used.
  Features Extraction. Binary features may be used as data representation—whether the word (or word-pair) exists in one of the DICOM text tags or not. Word frequencies may not have to be taken into account because usually in DICOM headers it does not really matter what is the frequency of the word appearance. Finally, since text tags usually include short text sequences, the raw text tags by themselves may also be used as features to the classifier.

The problem of pre-processing prediction may be treated as a multi-class classification problem. Formally, we are given a training set of the form (xi; yi) where xi is the ith series data and yi is an element of {alg1; alg2; . . . ; algN; NONE} is the ith class label. We aim to a learning model H such that H(xi)=yi.

For the classification task, a Random Forest classifier may be used which is an ensemble of classification trees. Each one of the trees may be built using bootstrap sample of data (bagging), and at each split the candidate set of variables is a random subset of the variables. Random Forests were widely used for Computer Vision applications, but also for other tasks such as Gene Selection. The inventors have recognized that they have several characteristics that make them a good fit for the data we are dealing with:
  Random Forest can be used when there are many more variables than observations. This may occur in the present case—there may be many word features (from the DICOM text tags) on one hand, and on the other it is desired for the classifier to work well even if we do not have a long history of processing algorithms usage to learn from.
  Random Forest has a good predictive performance even when most variables are noise, and therefore it does not require pre-selection of features. It has a built-in feature selection property, which may be very useful in the present case where we have many features out of which only a few may be really important for the problem at hand.

Random Forest classification is described by Breiman, L. "Random forests", Machine learning, 45(1), 5-32. (2001), which is hereby incorporated by reference in so far as describing the random forest classification. The Bag of Words data representation is described by Baeza-Yates, R. and Ribeiro-Neto, B. "Modern information retrieval", Vol. 463. New York: ACM press. (1999), which is hereby incorporated by reference in so far as describing the Bag of Words data representation.

Figure 5:
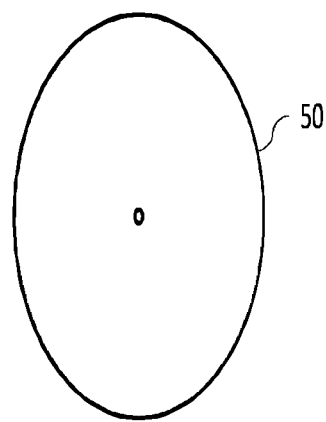
FIG. 5 schematically shows an exemplary embodiment of a software program product allowing a processor to carry out the method of the present invention.

FIG. 5 schematically shows a software program product 60 which contains instructions allowing a processor to carry out embodiments of the method of the present invention. The software program product 50 may contain a tangible carrier, such as a DVD, on which the instructions are stored. An alternative tangible carrier is a portable semiconductor memory, such as a so-called USB stick. In some embodiments, the tangible carrier may be constituted by a remote server from which the software program product may be downloaded, for example via the internet.

In embodiments of the present invention, dynamic supervised machine learning systems are used. Dynamic supervised machine learning systems are very suitable as they can adapt to changes over time, either changes in the data types or changes in the usage patterns.

The invention can be applied to many types of images, including but not limited to computer tomography (CT) images, X-ray images, magnetic resonance (MR) images, positron emission tomography (PET) images, and/or other images. Instead of AV processing, any other type of smart or other image data processing can be utilized.

Embodiments of a method of processing image data according to the invention may be summarized as automatically selecting an advanced visualization algorithm by using a feature vector and a machine learned model, applying the selected advanced visualization algorithm to the image data to produce advanced visualization data, receiving user input, and outputting the advanced visualization data if the user input matches the selected advanced visualization algorithm. If the user input fails to match the advanced visualization algorithm selected by the machine learned model, then the user input may be used to select another advanced visualization algorithm which may then be applied to the image data to produce advanced visualization data. The feature vector may include image features and/or metadata. In some embodiments, the feature vector may include only text data, such as DICOM data.

The invention is based upon the insight that the time required for image processing can be shortened by predicting which type of image processing will be carried out on a particular set of image data and by initiating any required pre-processing of the image data before the actual image processing is started.

Although the invention has been explained with reference to medical applications, the invention is not so limited and may also be used for industrial or defence applications, for example.

It will be understood that the description of the invention given above is not intended to limit the invention in any way. Singular nouns and the articles "a" and "an" are of course not meant to exclude the possibility of plurals. Devices mentioned in this document may be replaced with their successors, even if these successors are not yet known at the time of writing. As is well established in the law of patents, the abstract should never be used to limit the scope of the claims, and neither should reference numbers in the claims.

It will further be understood by those skilled in the art that the present invention is not limited to the embodiments mentioned above and that many additions and modifications are possible without departing from the scope of the invention as defined in the appending claims.

The invention claimed is:
1. A computer-implemented method of reducing processing time of an application for visualizing image data, wherein the application is one of a plurality of applications selectable by a user, wherein each of the plurality of applications comprises a pre-processing algorithm of a plurality of pre-processing algorithms for pre-processing the image data before image processing the selected application has started, wherein the method comprises predicting which one of the plurality of pre-processing algorithms is to be performed in response to a selection of one of the applications by the user by:
  extracting a feature vector from the image data, metadata, and/or additional data associated with the image data,
  supplying the feature vector as input to a machine learned model,
  receiving an algorithm identifier as output from the machine learned model, the algorithm identifier identifying the pre-processing algorithm,
  using the algorithm identifier to select the pre-processing algorithm, thereby obtaining a selected pre-processing algorithm, and
  pre-processing the image data using the selected pre-processing algorithm.

2. The method according to claim 1, wherein the image data is Digital Imaging and Communications in Medicine (DICOM) image data, wherein the metadata is a DICOM header of the DICOM image data, and wherein the extracting the feature vector comprises extracting DICOM text tags from the DICOM header.

3. The method according to claim 2, wherein the DICOM text tags are free-text DICOM tags, and wherein the extracting the feature vector comprises processing the free-text DICOM tags to obtain a set of processed DICOM text tags.

4. The method according to claim 3, wherein the extracting the feature vector comprises using a random forest machine learning technique to generate the feature vector from the set of processed DICOM text tags.

5. The method according to claim 1, wherein the machine learned model is produced by a machine learning system.

6. The method according to claim 5, wherein the machine learning system comprises a machine learning engine configured for building a machine learned model by using a feature vector as input vector and receiving at least one algorithm identifier as output vector, wherein the feature vector is extracted from the image data, metadata, and/or additional data associated with the image data.

7. The method according to claim 6, wherein the feature vector is extracted from the image data, metadata and/or additional data associated with the image data from a single picture archiving and communication system.

8. The method according to claim 1, wherein a processing algorithm is configured for leaving the image data unaltered.

9. A computer readable medium comprising transitory or non-transitory data representing instructions arranged to cause a processor to carry out the method according to claim 1.

10. The method according to claim 1 wherein the selected pre-processing algorithm generates at least one of measurements and 3D views of body parts from the image data.

11. The method according to claim 1 wherein the image data includes medical image data generated by a medical scanner selected from the group consisting of a computer tomography (CT) scanner, a magnetic resonance (MR) scanner, and an x-ray scanner.

12. A device configured for reducing processing time of an application for visualizing image data, wherein the application is one of a plurality of applications selectable by a user, wherein each of the plurality of applications comprises at least one of a plurality of pre-processing algorithms for pre-processing the image data before the actual image processing is started, the device comprising one or more processors configured to perform the method according to claim 1.

13. A device configured for reducing processing time of an application for visualizing image data, wherein the application is one of a plurality of applications selectable by a user, wherein each of the plurality of applications comprises at least one of a plurality of pre-processing algorithms for pre-processing the image data before actual processing of the image data is started, the device comprising:
  an input interface configured to access the image data, metadata, and/or additional data associated with the image data;
  a memory comprising application data representing the plurality of applications and instruction data representing a set of instructions; and
  a processor configured to communicate with the input interface and the memory and to execute the set of instructions, wherein the set of instructions, when executed by the processor, causes the processor to predict, in response to a selection of an application by the user, which one of the plurality of pre-processing algorithms is to be performed by:
    extracting a feature vector from the image data, metadata, and/or additional data associated with the image data,
    supplying the feature vector as input to a machine learned model, wherein the machine learned model is stored as model data in the memory,
    receiving an algorithm identifier as an output from the machine learned model, the algorithm identifier identifying at least one of the pre-processing algorithms,
  the set of instructions, when executed by the processor, further causing the processor to:
    use the algorithm identifier to select one or more of the pre-processing algorithms, thereby obtaining a selected one or more of the pre-processing algorithms, and
    pre-process the image data using the selected one or more of the pre-processing algorithms.

14. The device according to claim 13 being a workstation or imaging apparatus.

15. The device according to claim 13, wherein the selected one or more or more of the pre-processing algorithms generates at least one of measurements and 3D views of body parts from the image data.

16. The device according to claim 13, wherein the image data is generated by a CT scanner, an MR scanner, and an x-ray scanner.

17. A device configured for reducing processing time of a processing application for visualizing medical diagnostic image data, wherein the application is one of a plurality of pre-processing applications selectable by a user, wherein each of the plurality of applications includes one or more pre-processing algorithms for pre-processing the medical diagnostic image data, the device including one or more processors configured to:
  receive from an input interface the medical diagnostic image data, metadata, and/or additional data associated with the medical image data and one or more user selected applications;
  predict which one or more of the pre-processing algorithms is to be performed in response to the one or more user-selected applications by:

extracting a feature vector from the medical diagnostic image data, the metadata, and/or the additional data associated with the medical diagnostic image data, supplying the feature vector as an input to a machine learned model, and receiving one or more algorithm identifiers as an output from the machine learned model identifying one or more of the pre-processing algorithms;

use the one or more algorithm identifiers to select the one or more pre-processing algorithms; and pre-process the medical diagnostic image data using the one or more selected pre-processing algorithms.

18. The apparatus according to claim 17 wherein the one or more applications generates at least one of measurements and 3D views of a body part from the medical diagnostic image data.

\* \* \* \* \*